United States Patent
Mayer et al.

(10) Patent No.: US 10,572,627 B2
(45) Date of Patent: Feb. 25, 2020

(54) APPARATUS AND METHOD FOR OPTIMIZING TREATMENT USING MEDICATION COMPLIANCE PATTERNS AND GLUCOSE SENSOR

(71) Applicant: I.D. THERAPEUTICS LLC, Salem, WI (US)

(72) Inventors: Steven L. Mayer, Salem, WI (US); David C. Kravitz, Barrington Hills, IL (US); Tracey H. Mayer, Salem, WI (US)

(73) Assignee: I.D. THERAPEUTICS LLC, Salem, WI (US)

( * ) Notice: Subject to any disclaimer, the term of this patent is extended or adjusted under 35 U.S.C. 154(b) by 946 days.

(21) Appl. No.: 15/045,854

(22) Filed: Feb. 17, 2016

(65) Prior Publication Data

US 2016/0162659 A1 Jun. 9, 2016

Related U.S. Application Data

(63) Continuation of application No. 13/837,809, filed on Mar. 15, 2013, now abandoned.

(51) Int. Cl.
*G06F 19/00* (2018.01)
*G16H 10/60* (2018.01)
(Continued)

(52) U.S. Cl.
CPC ...... *G06F 19/3456* (2013.01); *A61B 5/14546* (2013.01); *A61B 5/411* (2013.01);
(Continued)

(58) Field of Classification Search
CPC .......... A61N 1/08; G06F 17/30; G06F 19/30; G06F 19/32; G06F 19/321; G06F 19/324;
(Continued)

(56) References Cited

U.S. PATENT DOCUMENTS 3,521,743 A 7/1970 Sposito
3,712,583 A 1/1973 Martindale et al.
(Continued)

FOREIGN PATENT DOCUMENTS

EP 1 075 831 A1 2/2001
NL 1 010 391 C2 4/2000
(Continued)

OTHER PUBLICATIONS

Jul. 2, 2014 International Search Report and Written Opinion issued in International Patent Application No. PCT/US2014/027931.
(Continued)

*Primary Examiner* — Maroun P Kanaan
(74) *Attorney, Agent, or Firm* — Oliff PLC

(57) ABSTRACT

Methods and apparatus monitor medication usage data for one patient or a population of patients, which can be processed to determine compliance patterns. Such methods and systems can associate, analyze, organize and present medication usage data, compliance patterns, and correlations between compliance patterns and outcomes data for electronic analysis or analysis by a caretaker. Such methods and apparatus permit analysis of compliance patterns to enable, for example, establishment or adjustment of safe and effective treatment regimens, and may include feedback systems for ensuring authenticity of medication and/or effects of medication on a patient. Such methods and apparatus also permit detection of medication in a biological sample of the patient through a medication monitor having a detection device, such as a skin-prick device, and a glucose sensor that can detect a target agent in the biological sample.

20 Claims, 4 Drawing Sheets

(51) Int. Cl.
  *G16H 15/00* (2018.01)
  *A61B 5/00* (2006.01)
  *A61B 5/145* (2006.01)
  *A61J 7/04* (2006.01)

(52) U.S. Cl.
  CPC ........... *A61B 5/4833* (2013.01); *A61J 7/0409* (2013.01); *A61J 7/0445* (2015.05); *A61J 7/0481* (2013.01); *G06F 19/3418* (2013.01); *G06F 19/3462* (2013.01); *G16H 10/60* (2018.01); *G16H 15/00* (2018.01); *A61J 7/0418* (2015.05); *A61J 7/0436* (2015.05); *A61J 2200/30* (2013.01); *A61J 2205/60* (2013.01)

(58) Field of Classification Search
  CPC .... G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 10/10; G06Q 40/08; G06Q 50/22; G06Q 50/24; G16H 10/00; G16H 10/20; G16H 10/40; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00; G16H 10/60; A61B 5/14532; A61B 5/1118; A61B 5/0077
  See application file for complete search history.

(56) References Cited

U.S. PATENT DOCUMENTS

| | | | |
|---|---|---|---|
| 3,845,974 A | 11/1974 | Pelloux-Gervais | |
| 3,881,990 A | 5/1975 | Burton et al. | |
| 4,504,153 A | 3/1985 | Schollmeyer et al. | |
| 4,939,705 A | 7/1990 | Hamilton et al. | |
| 5,013,303 A | 5/1991 | Tamari et al. | |
| 5,051,352 A | 9/1991 | Martindale et al. | |
| 5,149,321 A | 9/1992 | Klatz et al. | |
| 5,239,491 A | 8/1993 | Mucciacciaro | |
| 5,286,718 A | 2/1994 | Elliott | |
| 5,395,314 A | 3/1995 | Klatz et al. | |
| 5,405,742 A | 4/1995 | Taylor | |
| 5,408,443 A | 4/1995 | Weinberger | |
| 5,451,524 A | 9/1995 | Coble et al. | |
| 5,476,763 A | 12/1995 | Bacchi et al. | |
| 5,514,536 A | 5/1996 | Taylor | |
| 5,584,804 A | 12/1996 | Klatz et al. | |
| 5,585,399 A | 12/1996 | Hong et al. | |
| 5,599,659 A | 2/1997 | Brasile et al. | |
| 5,643,712 A | 7/1997 | Brasile | |
| 5,657,236 A | 8/1997 | Conkright | |
| 5,699,793 A | 12/1997 | Brasile | |
| 5,702,881 A | 12/1997 | Brasile et al. | |
| 5,709,654 A | 1/1998 | Klatz et al. | |
| 5,710,551 A | 1/1998 | Ridgeway | |
| 5,752,929 A | 5/1998 | Klatz et al. | |
| 5,843,024 A | 12/1998 | Brasile | |
| 5,850,344 A | 12/1998 | Conkright | |
| 5,852,408 A | 12/1998 | Christiansen et al. | |
| 5,852,590 A | 12/1998 | de la Huerga | |
| 5,879,329 A | 3/1999 | Ginsburg | |
| 5,894,266 A | 4/1999 | Wood, Jr. et al. | |
| 5,928,182 A | 7/1999 | Kraus et al. | |
| 5,950,632 A | 9/1999 | Reber et al. | |
| 5,954,641 A | 9/1999 | Kehr et al. | |
| 5,971,594 A | 10/1999 | Sahai et al. | |
| 5,983,193 A | 11/1999 | Heinonen et al. | |
| 6,046,046 A | 4/2000 | Hassanein | |
| 6,085,752 A | 7/2000 | Kehr et al. | |
| 6,102,855 A | 8/2000 | Kehr et al. | |
| 6,238,908 B1 | 5/2001 | Armstrong et al. | |
| 6,249,717 B1 | 6/2001 | Nicholson et al. | |
| 6,259,654 B1 | 7/2001 | de la Huerga | |
| 6,294,999 B1 | 9/2001 | Yarin et al. | |
| 6,300,875 B1 | 10/2001 | Schafer | |
| 6,380,858 B1 | 4/2002 | Yarin et al. | |
| 6,411,567 B1 | 6/2002 | Niemiec et al. | |
| 6,492,103 B1 | 12/2002 | Taylor | |
| 6,529,446 B1 | 3/2003 | de la Huerga | |
| 6,574,166 B2 | 6/2003 | Niemiec | |
| 6,604,650 B2 | 8/2003 | Sagar | |
| 6,642,045 B1 | 11/2003 | Brasile | |
| 6,673,594 B1 | 1/2004 | Owen et al. | |
| 6,751,730 B1 | 6/2004 | Walker et al. | |
| 6,961,285 B2 | 11/2005 | Niemiec et al. | |
| 6,994,954 B2 | 2/2006 | Taylor | |
| 7,002,476 B2 | 2/2006 | Rapchak | |
| 7,045,279 B1 | 5/2006 | Laske et al. | |
| 7,107,122 B1 | 9/2006 | Whyte | |
| 7,158,011 B2 | 1/2007 | Brue | |
| 7,269,476 B2 | 9/2007 | Ratnakar | |
| D552,739 S | 10/2007 | Green | |
| 7,295,890 B2 | 11/2007 | Jean-Pierre | |
| 7,304,913 B2 | 12/2007 | Niemiec et al. | |
| 7,545,257 B2 | 6/2009 | Brue | |
| 7,560,486 B2 | 7/2009 | Carpentier et al. | |
| 7,978,064 B2 | 7/2011 | Zdeblick et al. | |
| 8,323,954 B2 | 12/2012 | Kravitz et al. | |
| 2001/0028308 A1 | 10/2001 | De La Huerga | |
| 2002/0027507 A1 | 3/2002 | Yarin et al. | |
| 2002/0067270 A1 | 6/2002 | Yarin et al. | |
| 2002/0094949 A1 | 7/2002 | Paquin et al. | |
| 2002/0104848 A1 | 8/2002 | Burrows et al. | |
| 2003/0036683 A1* | 2/2003 | Kehr .................. G06F 19/325 |
| | | | 600/300 |
| 2003/0086338 A1 | 5/2003 | Sastry et al. | |
| 2003/0099158 A1 | 5/2003 | De la Huerga | |
| 2004/0038891 A1 | 2/2004 | Bisgaier et al. | |
| 2004/0133305 A1 | 7/2004 | Jean-Pierre | |
| 2004/0224298 A1 | 11/2004 | Brassil et al. | |
| 2005/0182653 A1 | 8/2005 | Urban et al. | |
| 2006/0124655 A1 | 6/2006 | Ratnakar | |
| 2006/0166182 A1 | 7/2006 | Weinberg et al. | |
| 2007/0016443 A1 | 1/2007 | Wachman et al. | |
| 2007/0039624 A1 | 2/2007 | Roberts et al. | |
| 2007/0073560 A1 | 3/2007 | Walker et al. | |
| 2007/0135691 A1 | 6/2007 | Zingelewicz et al. | |
| 2007/0156282 A1 | 7/2007 | Dunn | |
| 2008/0030309 A1 | 2/2008 | Darrouzet | |
| 2008/0054007 A1 | 3/2008 | Mador | |
| 2008/0059228 A1 | 3/2008 | Bossi et al. | |
| 2008/0077440 A1 | 3/2008 | Doron | |
| 2008/0099367 A1 | 5/2008 | Niemiec et al. | |
| 2008/0114490 A1 | 5/2008 | Jean-Pierre | |
| 2008/0167578 A1 | 7/2008 | Bryer et al. | |
| 2008/0195414 A1 | 8/2008 | Duckert | |
| 2008/0201168 A1 | 8/2008 | Brown | |
| 2008/0213904 A1 | 9/2008 | Sliwa et al. | |
| 2008/0281630 A1 | 11/2008 | Sekura | |
| 2009/0192648 A1 | 7/2009 | Namineni et al. | |
| 2010/0330547 A1 | 12/2010 | Tempelman et al. | |
| 2011/0183310 A1 | 7/2011 | Kravitz et al. | |
| 2012/0072231 A1 | 3/2012 | Mayer et al. | |
| 2012/0203573 A1 | 8/2012 | Mayer et al. | |
| 2012/0315618 A1 | 12/2012 | Kravitz et al. | |
| 2012/0315621 A1 | 12/2012 | Lu et al. | |

FOREIGN PATENT DOCUMENTS

| | | |
|---|---|---|
| WO | 98/38909 A1 | 9/1998 |
| WO | 2006/035278 A1 | 4/2006 |

(56) References Cited

FOREIGN PATENT DOCUMENTS

| WO | 2008/064134 A2 | 5/2008 |
|---|---|---|
| WO | 2008/079340 A2 | 7/2008 |
| WO | 2011150186 A1 | 12/2011 |
| WO | 2012163710 A1 | 12/2012 |
| WO | 2013/142801 A2 | 9/2013 |

OTHER PUBLICATIONS

Dolan, "Proteus receives patent for ingestible sensor", Jul. 14, 2011, http://mobihealthnews.com/11923/proteus-receives-patent-for-ingestible-sensor, pp. 1-6.

Apr. 27, 2012 International Search Report issued in International Application No. PCT/US2011/052522.

Apr. 27, 2012 Written Opinion of the International Search Authority issued in International Application No. PCT/US2011/052522.

Feb. 22, 2012 Invitation to Pay Additional Fees and Partial International Search Report issued in International Application No. PCT/US2011/052522.

Prendergast, Mary B. et al., "Optimizing Medication Adherence: An Ongoing Opportunity to Improve Outcomes After Kidney Transplantation," Clin J Am Soc Nephrol, vol. 5, pp. 1305-1311, 2010.

Chavers, Blanche M. et al., "Infection-Related Hospitalization Rates in Pediatric versus Adult Patients with End-Stage Renal Disease in the United States," Clin J Am Soc Nephrol, vol. 18, pp. 952-959, 2007.

Nevins, Thomas E. et al., "Quantitative Patterns of Azathioprine Adherence After Renal Transplantation," Clinical and Translational Research, vol. 87(5), pp. 711-718, Mar. 15, 2009.

Fredericks, Emily M. et al, "Adherence to immunosuppressants: how can it be improved in adolescent organ transplant recipients?," Pediatric Transplantation, vol. 15, issue 5, pp. 614-620, Oct. 2010.

Cravedi, Paolo et al., "Noninvasive Methods to Assess the Risk of Kidney Transplant Rejection," Expert Review of Clinical Immunology, vol. 5(5), pp. 535-546, 2009.

Schäfer-Keller, P. et al., "Non-Adherence measurement in kidney transplantation," American Journal of Transplantation, vol. 8(3), pp. 616-626, 2008.

Denhaerynck, K. et al., "Prevalence and risk factors of non-adherence with immunosuppressive medication in kidney transplant patients," American Journal of Transplantation, vol. 7, pp. 108-116, 2007.

Vrijens et al.; "Adherence to prescribed antihypertensive drug treatments: longitudinal study of electronically compiled dosing histories," BMJ published online May 14, 2008; doi:10.1136/bmj.39553.670231.25.

Vrijens, Bernard et al., "Successful Projection of the Time Course of Drug Concentration in Plasma During a 1-Year Period from Electronically Compiled Dosing-Time Data Used as Input to Individually Parameterized Pharmacokinetic Models," Journal of Clinical Pharmacology, 2005, 45:1-000, pp. 1-7.

Vrijens, Bernard et al., "Adherence to Prescribed Antihypertensive Drug Treatments: Longitudinal Study of Electronically Compiled Dosing Histories," BMJ.com, downloaded May 15, 2008, pp. 1-6.

"The SIMpill Medication Adherence Solution," 2008, pp. 1, http://www.simpill.com/thesimplesolution.html.

"How the SIMpill Medication Adherence Solution Works," 2008, pp. 1-2, http://www.simpill.com/howsimpillworks.html.

"Products—On-Cue Compliance Service," 2006, pp. 1-2, http://www.simpill.com/p-occs-main.html.

Rushi Gandhi, James Vi, Jihyen Ha, Hang Shi, Ola Ismail, Sahra Nathoo, Joseph V. Bonventre, Xizhong Zhang, Lakshman Gunaratnam, "Accelerated receptor shedding inhibits kidney injury molecule-1 (KIM-1)-mediated efferocytosis" Am J. Physiol. Renal Physiol., Jul. 15, 2014,307(2), pp. F205-F221. 001: 10.1152/ajprenal.00638.2013.

Xiang, Y and Lu, Y "Using personal glucose meters and functional DNA sensors to quantify a variety of analytical targets" Nat Chem. Jul. 24, 2011; 3(9): 697-703 and supplemental information (S1-S17). 001: 10.1 038/nchem.1 092.

Valion, V; Muhlbauer, B; Osswald, H "Adenosine and Kidney Function" Physiol Rev 86: 901-940, 2006; doi:10.1152/physrev.00031.2005.

Vaidya et ai, "Urinary Kidney Injury Molecule-1: A Sensitive Quantitative Biomarker for Early Detection of Kidney Tubular Injury" X Am. J. Physiol. Renal Physiol., 2006 (pub online Sep. 20, 2005), 290, pp. F517-529, doi:1 0.1152/ajprenal.00291.2005.

Bailly, V, et al "Shedding of Kidney Injury Molecule-1, a Putative Adhesion Protein Involved in Renal Regeneration" J. Biol. Chem., Oct. 18, 2002,277, pp. 39739-39748, doi: 10.1 74/jbc.M200562200.

Bonventre J.V., "Kidney injury molecule-1 (KIM-1): a urinary biomarker and much more," Nephrology Dialysis Transplantation, vol. 24, No. 11, Mar. 23, 2009, pp. 3265-3268.

Nijboer W.N. et al., "Kidney Injury Molecule-1 is an Early Non-invasive Indicator for Donor Brain Death-Induced Injury Prior to Kidney Transplantation," American Journal of Transplantation, vol. 9, No. 8, Aug. 1, 2009, pp. 1752-1759.

Sabbisetti V.S. et al., "Novel Assays for Detection of Urinary KIM-1 in Mouse Models of Kidney Injury," Toxicological Sciences, vol. 131, No. 1, Sep. 27, 2012, pp. 13-25.

Aug. 5, 2014 International Search Report issued in International Patent Application No. PCT/US2014/027998.

Aug. 5, 2014 Written Opinion issued in International Patent Application No. PCT/US2014/027998.

Sep. 15, 2015 International Preliminary Report on Patentability and Written Opinion issued in PCT/US2014/027998.

Sep. 28, 2012 International Search Report issued in PCT/US2012/041257, 3 pages.

Sep. 28, 2012 Written Opinion issued in PCT.US2012/041257, 8 pages.

Jochmans, Ina et al., "Graft Quality Assessment in Kidney Transplantation: Not an Exact Science Yet!" Current Opinion in Organ Transplantation, Apr. 2011, pp. 174-179, vol. 16, No. 2, Lippencott Williams & Wilkins.

Moers, Cyril et al., "The Value of Machine Perfusion Perfusate Biomarkers for Predicting Kidney Transplant Outcome," Transplantation, Nov. 2010, pp. 966-973, vol. 90, No. 9, Lippincott Williams & Wilkins.

\* cited by examiner

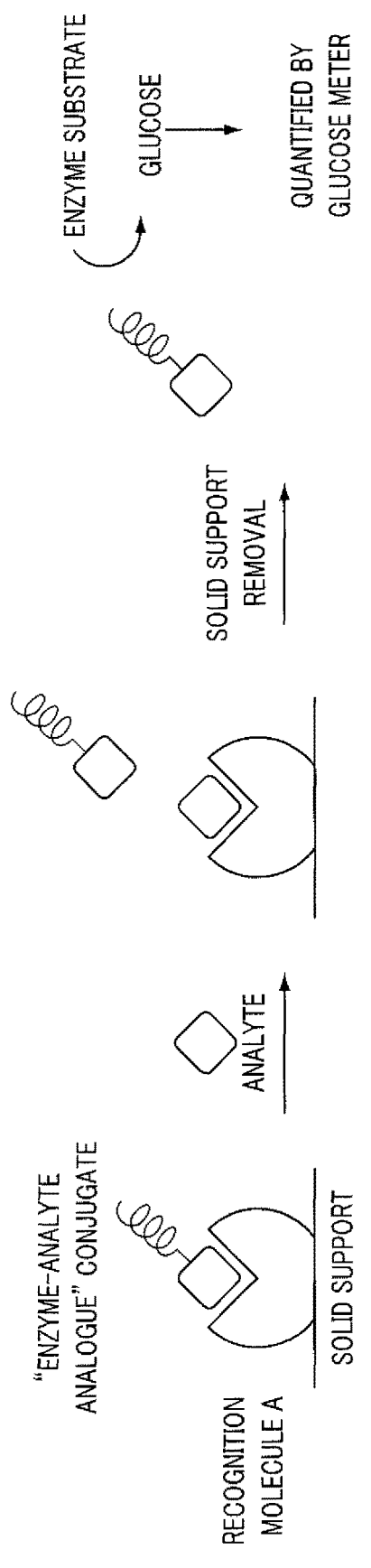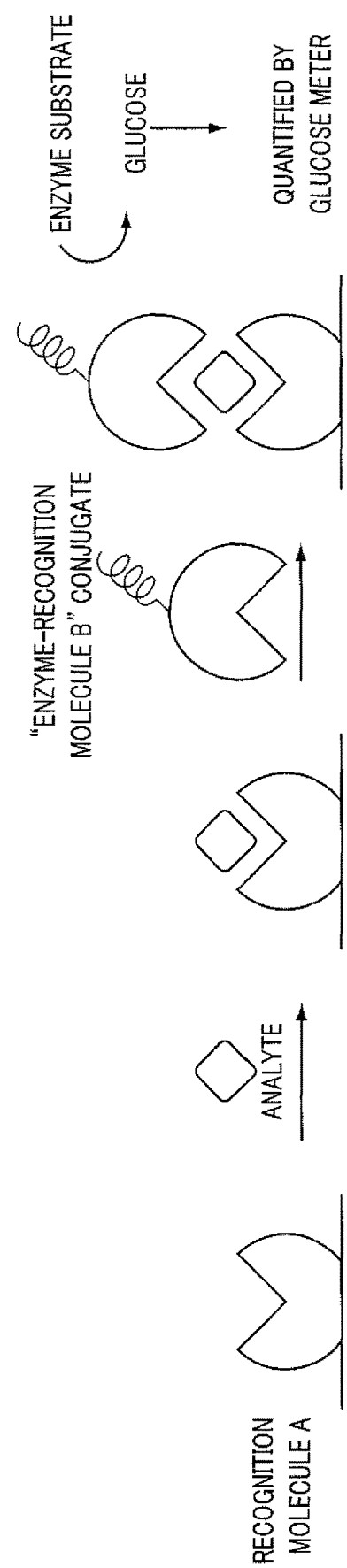
FIG. 2A
FIG. 2B

APPARATUS AND METHOD FOR
OPTIMIZING TREATMENT USING
MEDICATION COMPLIANCE PATTERNS
AND GLUCOSE SENSOR

This is a Continuation of application Ser. No. 13/837,809 filed Mar. 15, 2013. The entire disclosure of the prior application is hereby incorporated by reference herein in its entirety.

BACKGROUND

The disclosure relates to methods and apparatus for monitoring, storing, and analyzing patient medication usage data and compliance patterns involving use of a sample testing device, associating compliance patterns with medication properties data and patient history data, and for determining a correlation between medication compliance patterns and other data.

Medications may include potent chemical and/or biological elements designed to induce a specific ameliorative effect on a patient's disease state or medical condition. Medication manufacturers, prescribing physicians, and caretakers have limited information about a given medication that typically includes only basic guidelines for safely and effectively prescribing very powerful substances to patients.

This dearth of information is especially significant with regard to the effects of medication treatment regimen compliance. Medication manufacturers, prescribing physicians and other caretakers struggle to effectively manage the effects on patients of non-compliant medication intake or compliance patterns. For example, without data regarding patient medication usage, caregivers face difficulty discerning whether negative effects of medication intake are the result of precise, over, or under compliance by the patient, or a prescribed treatment regimen that is ineffective or unsafe. There are few or no independent objective measures of a patient's actual compliance with a prescribed treatment regimen, aside from the patients' memory about their own historical medication compliance over time. Further, there are few or no independent objective measures of negative or ameliorative effects attributable to varying degrees of over and/or under compliance with treatment regimens.

Poor or unexpected medication treatment regimen compliance is a medical problem that poses risks to patient health and potentially increases health care costs. By way of example, a patient who has undergone an organ transplant may be prescribed a regimen of immunosuppressive medications to protect the patient's transplanted organ from being rejected by the patient's immune system. If a patient takes too much or too little of these medications, or takes them at incorrect time intervals, then the patient's body may experience a cascade of biochemical reactions that may result in the transplanted organ being rejected or other diseases being acquired, or other complications.

For example, if a patient takes too much of an immunosuppressive medication, even intermittently, the patient's inherent immunological capability may be adversely affected, thereby rendering the patient susceptible to malignancies, bacterial infections and viral infections. The complications of an over-suppressed immune system can lead to death, severe illness that requires hospitalization, and can compromise the transplanted organ. The medical intervention often expended to redress such adverse consequences can add significant direct and indirect financial costs for the patient and the health care system, in addition to potentially limiting the patient's quality of life.

SUMMARY

Methods and apparatus are needed that provide robust checks and balances for establishing medication regimens, adjusting medication regimens, and caring for patients who are taking medications, especially for those taking immunosuppressive medication. Further, methods and apparatus are needed that permit monitoring, analysis, and recording of medication usage data and regimen compliance patterns for individual patients and patient populations. Further still, methods are needed that permit analysis of medication regimen compliance patterns in view of patient history data to enable, for example, medication manufacturers and/or prescribing caretakers to safely and efficaciously establish and adjust treatment regimens.

Methods and apparatus are also needed that allow a user of a medication, and especially an immunosuppressive medication, to quickly, conveniently and efficiently monitor and manage medication usage data so that such data can be used for the treatment of that patient and/or a population of patients. Such methods and apparatus may include determining medication usage data by means of a detection device that is configured to detect a target agent in a biological sample by converting a substance to glucose and then detecting the presence and/or amount of the detected glucose.

U.S. Patent Application Publication No. 2012/0072231 discloses methods, systems, and apparatus for monitoring patient medication usage, determining medication compliance patterns, and establishing and adjusting medication regimens. The disclosure of U.S. Patent Application Publication No. 2012/0072231 is hereby incorporated by reference in its entirety.

BRIEF DESCRIPTION OF THE DRAWINGS

FIGS. 2A and 2B are schematic drawings showing exemplary mechanisms of target agent (analyte) detection using a glucose sensor based on the interaction between recognition molecule A, recognition molecule B and the target agent.

DETAILED DESCRIPTION OF EMBODIMENTS

Figure 1:
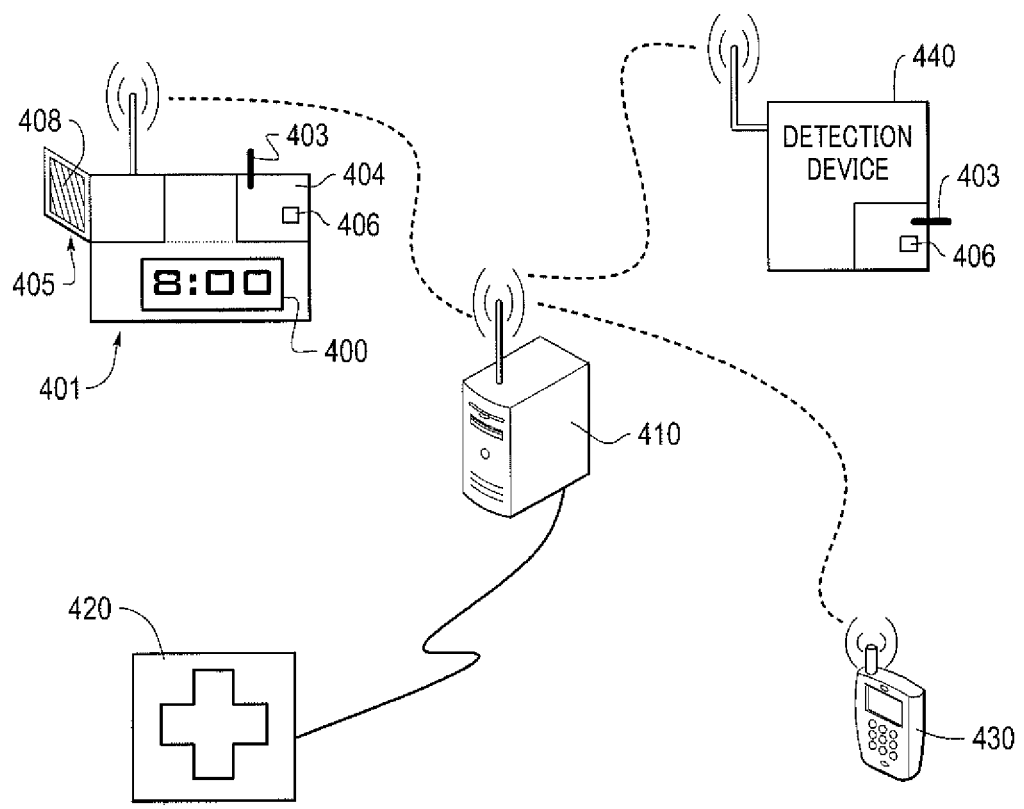
FIG. 1 is a perspective view of a medication monitor cartridge compartment in accordance with an exemplary embodiment.

It is desirable to provide a medication monitor that can detect both usage of medication and an amount and/or quantity of a target agent in a biological sample, through the use of a glucose sensor that is operatively connected to the medication monitor to generate medication usage data. It is also desirable to then communicate that medication usage to the patient, a caregiver, and/or a data network to generate and adjust treatment regimens based on the medication usage data.

According to exemplary implementations, a medication monitor for producing medication usage data may include a housing and a detection device operatively associated with the medication monitor. The detection device may include a sensor for detecting a target agent in a biological sample from a user. For example, the biological sample may be body fluid such as one or more of blood, urine and saliva. A preferred detection device may be a skin-prick device such as a finger-prick device. The detection device may be hard wired to the medication monitor or may be wirelessly connected to the medication monitor. The sensor may include a solid support to which is attached a recognition molecule that specifically binds to the target agent in the presence of the target agent but not significantly to other agents. The sensor may also include a substance that can be enzymatically converted to glucose and an enzyme that can catalyze the conversion of the substance to glucose. The enzyme may attach directly or indirectly to the recognition molecule such that in the presence of the target agent the enzyme can convert the substance into glucose. The medication monitor may include a processor that produces medication data based on an amount of glucose sensed and may include a communications port configured to communicate the medication data.

According to some embodiments the housing body may include a housing for containing medication or medication packaging. The housing body may define an opening to accommodate insertion and removal of medication or medication packaging. The housing body may also include a lid that opens (e.g., by sliding, pivoting or removal) to removably cover the opening. A medication sensor may be provided that is configured to sense identity of the medication. A removal sensor may also be provided that senses medication or medication packaging removal or device opening. The processor, in addition to producing medication data based on the amount of glucose sensed, may also produce medication usage data based on the sensed removal. The medication sensor and the removal sensor may be provided to monitor patients' compliance with treatment regimens by keeping track of the medication in the medication monitor. Medication data and medication usage data may be correlated by way of one or more processor onboard the medication monitor and/or in an external data network with which the medication monitor can communicate.

According to exemplary embodiments, the target agent may be an immunosuppressant detected in a biological sample, such as the user's blood, such as Tacrolimus, or a metabolite thereof. The enzyme may be attached to a Tacrolimus analogue molecule that competes less strongly than Tacrolimus or a metabolite thereof for binding to the recognition molecule. Alternatively, the enzyme may be attached to a molecule that binds to Tacrolimus or a metabolite thereof that binds to the recognition molecule.

Examples of the solid support may include a bead or a membrane. The recognition molecule may include a nucleic acid molecule, a protein, a polymer, or an antibody that specifically binds to the target agent. The enzyme, for example, may be an invertase, sucrase or sucrase-isomaltase that can convert sucrose to glucose, a maltase that can convert maltose into glucose, a trehalase that can convert trehalose into glucose, an amylase that can convert starch into glucose, or a cellulase that can convert cellulose into glucose. Preferably, the enzyme is invertase. The sensor may include a plurality of sensors with each sensor of the plurality of sensors sensing a target agent specific to that sensor. Different ones of the plurality of sensors may each detect the same target agent or different target agents. An example of a sensor that quantitatively detects a target agent by detecting glucose is disclosed in U.S. Patent Application Publication No. 2012/0315621, which is hereby incorporated by reference in its entirety.

The medication monitor may include a communications port that is configured to wirelessly communicate the medication usage data to a data network to monitor compliance patterns and/or interacting between compliance patterns and sample levels of the target agent(s).

The medication monitor may include a sensor to detect, for example, an origin of manufacture of the pre-filled medication insert. Each pre-filled medication insert may have a barcode, RFID tag or other identifier that relays the origin of manufacture data and/or other data to verify authenticity of the medication. The monitor may include a reader such as a barcode reader, an RFID label reader or other information detector that verifies that the medication is not counterfeit or is otherwise a desired mature form and/or dosage of the medication at the time the medication monitor is loaded and/or at the time of use by the patient. The RFID information may also be sent to a receiving system such as a remote server, which verifies, and may send a signal to the monitor and/or another receiver, regarding whether the medication is appropriate. The monitor may also or instead include a sensor to detect a specific shape of a medication, the specific shape of the pre-filled medication insert, a medication made by a unique manufacturing process, or an orientation of the medication within the housing body to determine whether the medicine correctly loaded into the monitor and is not counterfeit or otherwise inappropriate.

Embodiments include methods that may accommodate optimizing treatment of a patient such as a transplant recipient or a population of such patients. Methods may include generating usage data regarding a patient's compliance with a medication treatment regimen with a medication monitor. Methods may include providing the usage data to a central server over a predetermined period of time, and determining the patient's pattern of compliance with the treatment regimen. Methods may include obtaining test results from a detection device, those test results being indicative of a target agent such as the medication or a metabolite of the medication, by collecting a biological sample with a detection device that is operatively connected to the medication monitor, and sensing the target agent with a target agent sensor provided with the detection device.

Target agent presence and/or levels (medication data) can then be correlated in one or more processor in the medication monitor and/or in a data network with which it can communicate. The sensor may comprise a solid support to which may be attached a recognition molecule that permits detection of the target agent, wherein the recognition molecule specifically binds to the target agent in the presence of the target agent but not significantly to other agents. The sensor may also include a substance that can be enzymatically converted to glucose, and an enzyme that can catalyze the conversion of the substance to glucose in the presence of the target agent.

Methods may include detecting the glucose produced from the substance with a glucosimeter to generate the medication data. The detection of glucose may indicate a presence of the target agent in the biological sample, and may also indicate levels of target agent in the biological sample, and an absence of detected glucose may indicate an absence of the target agent in the biological sample. Methods may also include correlating the patient's pattern of compliance with the medication data from the detection device, and outputting at least one recommendation from the above-mentioned processor(s). The recommendation may include replacing at least one medication used in the treatment regimen with at least one different medication, changing at least one dosage of at least one medication used in the treatment regimen, changing the timing of recommended usage of at least one medication in the treatment regimen, not changing the treatment regimen, and/or taking action to improve the patient's compliance.

Methods may also include correlating the patient's pattern of compliance and medication data with patterns of compliance and medication data from a population of patients, and outputting the at least one recommendation based on both the patient's pattern of compliance and medication data and the patterns of compliance and medication data from the population of patients. The treatment regimen may be a standardized treatment regimen or an individual patient treatment regimen.

Exemplary methods may include comparing the patient's compliance pattern with the medication data, and, based on the comparison, outputting a recommendation of replacing an immunosuppressant medication used in the treatment with a different medication, changing a dosage amount and/or frequency of an immunosuppressant medication, or not changing the regimen.

According to exemplary implementations, a self-contained medication monitor for producing medication usage data may be provided. The self-contained medication monitor may include a housing body, a first detection device for detecting removal of medication from the self-contained medication monitor and a second detection device operatively connected to the medication monitor and having a target agent sensor for detecting a target agent in a biological sample from a user. The target agent sensor may comprise a solid support to which is attached a recognition molecule that specifically binds to the target agent in the presence of the target agent but not significantly to other agents, a substance that can be enzymatically converted to glucose, and an enzyme that can catalyze the conversion of the substance to glucose. The enzyme may attach directly or indirectly to the recognition molecule, and in the presence of the target agent the enzyme can convert the substance into glucose. The self-contained medication monitor may also include a processor that produces information and/or recommendations based on detected removal of the medication and an amount of glucose sensed, and that outputs the information and/or recommendations to the patient or a caregiver. The processor may also output a recommendation to a health care provider, and may assist the health care provider in determining target drug levels or benchmark drug levels. The processor may output raw glucose concentration data, compare the amount glucose sensed with a pre-determined or other baseline glucose level, and/or quantitatively determine the amount of the target agent present in the biological sample based on a difference between the baseline glucose level and the amount of glucose sensed. The self-contained medication monitor may also include a display device configured to display the information and/or recommendations to the patient. Such recommendations may include, for example, a reminder to take a medication in accordance with a pre-established regimen, a recommendation to expedite or delay a dose of medication, and/or a recommendation to consult with a caregiver. In comparison to current tests, where the patient must visit his or her healthcare provider to have a drug level test conducted, methods using such a device are more convenient, may be performed more often, may be more closely tied to direct feedback from when the drug was taken, and may be measured independently of when the last drug was taken. For example, a drug dose does not have to be delayed while a patient visits the doctor's office to have drug level tests done.

FIG. 1 shows a treatment regimen compliance monitoring system having a medication monitor 401, and a receiving system 410. The receiving system 410 may be in communication with a storage system such as, for example, a server 420. The receiving system 410 may also be in communication with, for example, a reporting system 430. The receiving system 410 may also be in communication with a detection device 440. Any or all of the receiving system 410, the medication monitor 401, the server 420, the detection device 440, and the reporting system 430 may communicate by a wireless connection, wired connection, or a combination thereof, over the internet, local area network, PSTN, or the like. Medication monitor 401 may include a lid 405 having a transparent window 408. FIG. 1 shows the receiving system 410 as separate from the medication monitor 401, but they could be combined in a single device. The transparent window 408 may enable viewing of a medication contained by the medication container 401. Further, medication monitor 401 may be constructed to house multiple medications separately or together, and may be configured to separately monitor each of the housed medications. Medication monitor 401 may be constructed to house one or more medications in various dosage forms. For example, medication monitor 401 may be constructed to house and dispense oral suspension, injection, inhalation, gel, cream, capsule and/or solid dosage forms.

The medication monitor 401 may also include a detection device 404, and/or be usable with detection device 440. The detection device 404/440 includes a detection portion 403 and at least one glucose sensor 406 that is used to detect the presence and/or level of a target, such as a target analyte/agent in a biological sample from the user. Exemplary biological samples may include blood, serum, plasma, urine or saliva. The detection portion 403 may, for example, include a skin-prick device that can collect a sample of the user's blood after a pin prick anywhere on the user's body. The skin prick device could, for example, be a finger-prick device that obtains a sample of the user's blood after a finger-prick. The glucose sensor 406 includes a recognition molecule that is specific for the target agent, preferably attached to a solid support, and an enzyme that can catalyze the conversion of a substance into glucose (for example in the presence of the target agent). The enzyme can attach directly or indirectly to the recognition molecule. Although only one detection device 404/440 is illustrated in FIG. 1, it is understood that the detection device 404/440 may include a plurality of glucose sensors 406 and/or detection portion 403. The glucose sensors 406 may be configured to detect the same target agent or may each detect a different target agent found in the biological sample.

FIGS. 2A and 2B provide an overview of the glucose sensor 406 and exemplary methods of its use by respective competition and sandwich assay methods. In FIGS. 2A and 2B, the recognition molecule A and recognition molecule B (a recognition molecule that can bind to the target agent with high specificity) can be the same or different molecules, wherein both can bind to the analyte (referred to herein as the target agent). The enzyme that can catalyze the conversion of a substance (enzyme substrate) into glucose is conjugated with an analyte analogue (that is, an analogue of the target agent; FIG. 2A) or another recognition molecule B (FIG. 2B) to form enzyme-analyte analogue conjugate (FIG. 2A) or enzyme-recognition molecule B conjugate (FIG. 2B), respectively. A substrate provided in the detection device 404 can be catalytically converted into glucose by the enzyme, and the glucose produced can be detected and/or quantified by a glucose meter. The target agent (analyte) can be any substance that can be recognized by recognition molecule A or recognition molecule B.

FIG. 2A shows, for example, a release-based assay. Initially, enzyme-analyte analogue conjugate binds to the solid support through the interaction between enzyme-analyte analogue conjugate and recognition molecule A. When samples containing the target agent are applied to the solid support, the enzyme-analyte analogue conjugate will be released as a result of the competition between enzyme-analyte analogue conjugate and target agent in binding with recognition molecule A. The concentration of enzyme-analyte analogue conjugate released can be proportional to the target agent concentration in the sample. After removal of the solid support, enzyme-analyte analogue conjugate remaining in the solution can catalyze the conversion of the substrate into glucose, which is detected by a glucose meter, and the readout can be proportional to the analyte concentration.

FIG. 2B shows, for example, a binding-based assay. Initially, recognition molecule A is immobilized to the solid support. When a sample containing or suspected of containing the target agent (analyte) is applied to solid support, the analyte binds to recognition molecule A. Subsequently, enzyme-recognition molecule B conjugate is added and will bind to analyte that is bound to the recognition molecule A, forming a sandwich structure. The amount of enzyme-recognition molecule B conjugate bound can be proportional to the concentration of analyte in the sample. After applying the substrate (e.g., sucrose) to the solid support, the bound enzyme-recognition molecule B conjugate can convert substrate into glucose, which is detected by a glucose sensor such as a glucose meter, and the readout can be proportional to the analyte concentration. In this way, in the presence of more target agent, more enzyme will be bound to the solid support, and the solid support can convert more sucrose into glucose, giving a larger readout in glucose meter.

The glucose meter may be any medical device for determining the approximate concentration of glucose in a sample. Glucose meters, such as a personal glucose meter (PGM), typically display the level of glucose in mg/dl or mmol/l. This disclosure is not limited to a particular brand of glucose meter, though examples include ACCU-CHEK®, ONETOUCH®, PRODIGY®, ADVOCATE®, AGAMATRIX®, ASCENSIA®, BIONIME®, CLEVERCHEK®, EASYGLUCO®, FREESTYLE®, MAXIMA®, MEDISENSE® PRESTIGE®, TRUEBALANCE®, TRUETEST®.

Different types of recognition molecules, enzymes, solid supports, etc. and their different binding configurations are described, for example, in U.S. Patent Application Publication No. 2012/0315621, which is incorporated by reference in its entirety.

The glucose sensor 406 can be used to detect any target agent of interest. Thus, the methods and devices provided herein can be used to detect any target agent of interest, such as the specific examples provided herein. Selecting an appropriate recognition molecule that permits detection of the target agent allows one to develop a sensor that can be used to detect a particular target agent. One example of a target agent as an immunosuppressant is Tacrolimus or a metabolite thereof. Recognition molecules could be antibodies (monoclonal or polyclonal) or aptamer based. The antibodies or aptamers have specificity to the target agent. They can be produced by known methods of antibody or aptamer production or can be purchased from OEM suppliers. However, one skilled in the art will appreciate that other target agents can be detected with the disclosed sensors and devices using the disclosed methods. For example, the other target agents could be any of the substances discussed, for example, in paragraphs [0078]-[1010] of U.S. Patent Application Publication No. 2012/0072231, which is hereby incorporated by reference in its entirety.

As seen in FIG. 1, the medication monitor 401 may include a display 400. The display 400 may be, for example, a liquid crystal display that functions to present data generated or received by the medication monitor 401, or other information. Lid 405 may alternatively or additionally include a display 400. The lid 405 may be constructed to slideably and/or hingedly move between an open state and a closed state to accommodate access to and closure of one or more compartments of the medication monitor 401, thereby enabling a user to view the display while viewing and/or accessing at least one compartment of the medication monitor 401.

The medication container 401 may be battery powered, may include a SIM card, and/or may be GPS enabled. Medication container 401 may be a micro-electronic "smart" pill box that accepts a unique compartmentalized pill container insert that can either be hand-loaded with individual dosage forms of medications, or alternatively, the pill box can accept a custom designed, pre-filled cartridge. The pre-filled cartridge may include RFID or other labels that the medication container 401 can read to confirm the identity and/or amount of the medication contained in the pre-filled cartridge as an anti-counterfeiting measure to determine whether the pre-filled cartridge is authentic. Medication container 401 may be constructed to contain one or more types of medications that are each compartmentalized for ease of patient identification, dispensing, and refilling. The medication container 401 may, for example, be constructed of aesthetically and ergonomically designed injection molded thermoplastic. The medication container itself and/or a cartridge/magazine for it may be childproof or tamperproof, and/or the monitor may be usable with childproof and/or tamperproof containers. The childproof/tamperproof features may be mechanical, electronic, electromechanical or other. For example, they may involve one or more biometric identification features, such as a fingerprint recognition lock, and/or electronic codes, and may optionally include time lock features to help control untimely or excess access to the contained medication.

Figure 3A:
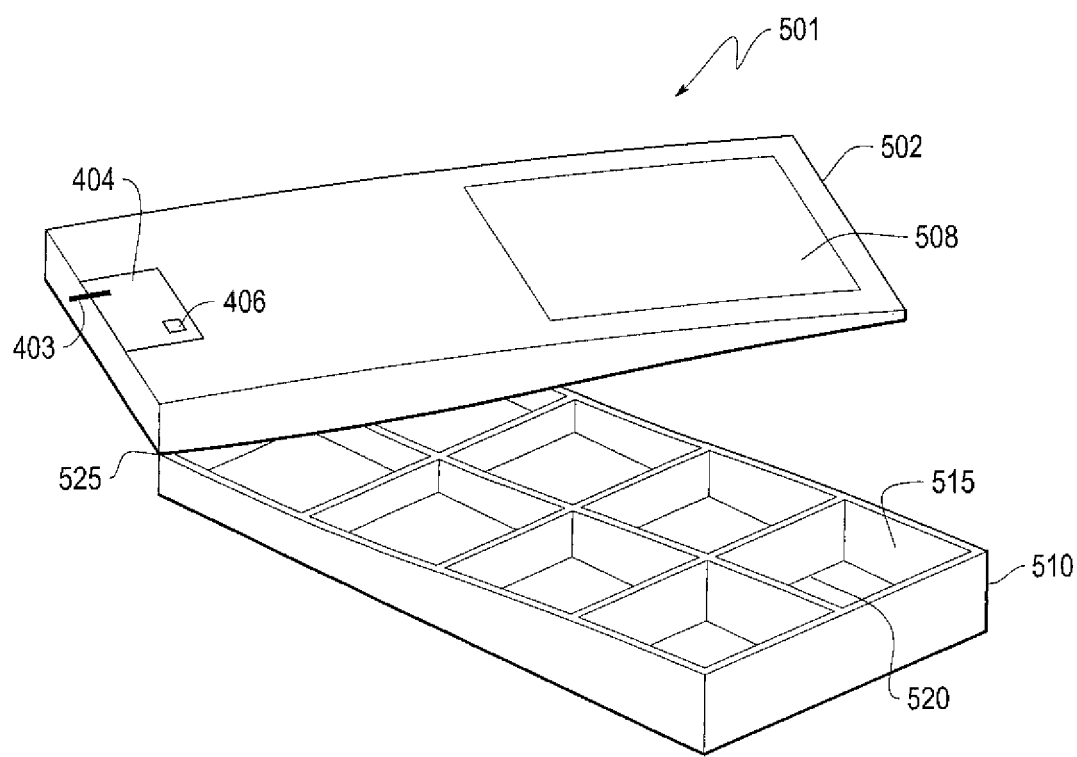
FIGS. 3A and 3B are perspective views of a medication monitor in accordance with an exemplary embodiment.

FIG. 3A shows a medication monitor 501 having a body 510. The body 510 may include a housing 515. The housing 515 may include one or more compartments 520. The medication monitor 501 may include a lid 502. The lid 502 may include a display 508. The display 508 may be, for example, a liquid crystal display, or any other suitable display now known or later developed. The lid 502 may be attached to the body 510 with a pivot 525 whereby the lid 502 may slideably move to cover or uncover the housing 515 of the body 510. The medication usage monitor 501 may have a detection device 404 that includes a detection portion 403 and at least one glucose sensor 406.

Figure 3B:
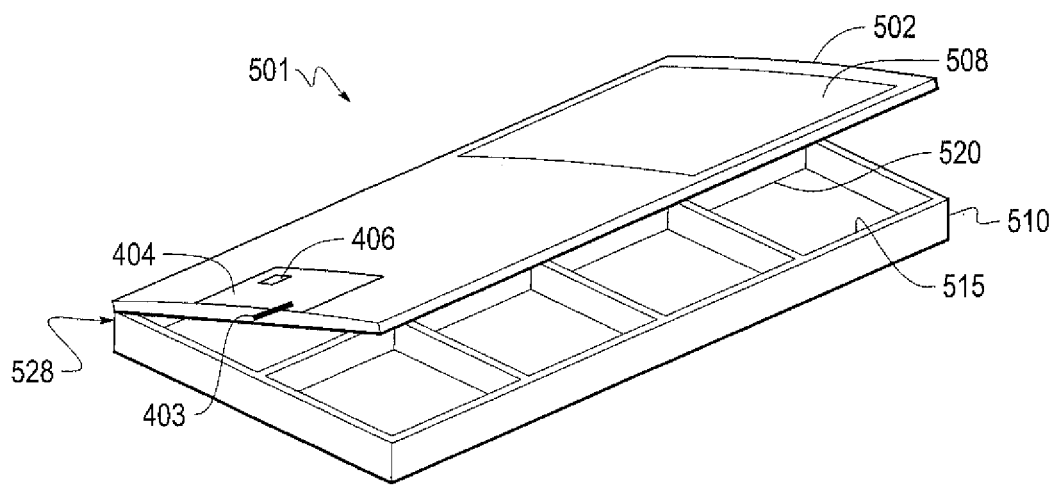

FIG. 3B shows medication monitor 501, which may include a lid 502. The lid 502 may include a display 508. The display may be, for example, a liquid crystal display, or any other suitable display now known or later developed. The lid 502 may be attached to the body 510 by a hinge 528 so that the lid 502 may be lifted upward with respect to the body 510 to provide access to the housing 515 and one or more compartments 520 located therein. The housing 515 may be constructed to receive and retain medication dosage forms, medication containers, medication cartridges that are factory refilled and/or refillable by consumers, and/or blister packs containing medication. One or more sensor may be provided to determine when medication is removed from the housing; such sensors may be specific to opening of or dosage removal from a single compartment, or from any of several compartments. Similar to the FIG. 3A, the detection monitor 501 illustrated may include a detection device 404 that includes a detection portion 403 and at least one glucose sensor 406.

The medication monitor 501 may serve as a periodic dispensing device. The medication monitor 501 may also serve as a monitor for determining medication refill needs and communicating related messages. The medication monitor 501 may be one unit or multiple units, and may include multiple containers or compartments for organizing multiple medications. If multiple units are provided to a single patient, they preferably are capable of communicating, and programmed to communicate, with one another to ensure integrated reporting of usage data. The medication monitor 501 may be sized to fit in a pocket, or a purse, or may be larger. The medication monitor 501 may be constructed to hold and organize portable medication monitors. It may optionally include one or more processors as described above.

The medication container 401 may include on-board micro-processing technology. The on-board micro-processing technology may function to record and/or report at least one of a time, a date, and a location of when a medication is inserted or removed, or a pre-loaded cartridge is inserted or removed, and/or other information as discussed herein. The micro-processing technology may function to record the number of medications or dosage forms in a specific medication compartment at any given time. The micro-processing technology may record a date, a location, and/or a time when the lid 408 is opened, and the date, the location, the time, and/or the amount when specific medication is removed or inserted. The micro-processing technology may function to determine medication compliance patterns and medication data, establish or recommend adjustment of treatment regimens in view of compliance data, medication properties data, medication data, and patient history data, and determine correlations among them, or those functions may be performed at a remote location.

Medication container 401 may include a transmitter 412 that effects communication of medication usage data, medication data, compliance patterns or other information discussed herein generated by the medication container 401, including medication usage data based on an output from the glucose sensor 406. The transmitter may effect communication to at least one of the receiving device 410 and the server 420. The communication may comprise the information generated or recorded by the micro-processing technology of the medication monitor 401, the detection device 440, and/or other information input by a patient or caregiver. Medication monitor 401 may include a port for communicating data, for example, wirelessly or by a Universal Serial Bus connection.

Information may be transmitted from the monitor 401 to a receiving system 410. The receiving system 410 may include a communications port such as a transceiver for receiving information and transmitting information to the reporting system 430 and/or the server 420. The receiving system 410 may include, for example, a port for communicating wirelessly or over a Universal Serial Bus connection. The receiving system 410 may include a remote storage system that receives and stores information from at least one of the medication monitor 401 and the receiving system 410. The receiving system 410 and/or remote storage device may implement algorithms to analyze information such as medication usage data, established treatment regimen data, medication properties data, medication data, and patient history data, including outcomes data. Outcomes data may be received by receiving system 410 from, for example, server 420 or a healthcare provider, whether private or publicly accessible. A monitored patient's attending physician, healthcare system representative, or laboratory information system, a data collection center, or the like may electronically provide a patient's outcomes data to the receiving system. Medication properties data such as medication interaction data may be received from a central database or other repository of medication interaction data.

Figure 4:
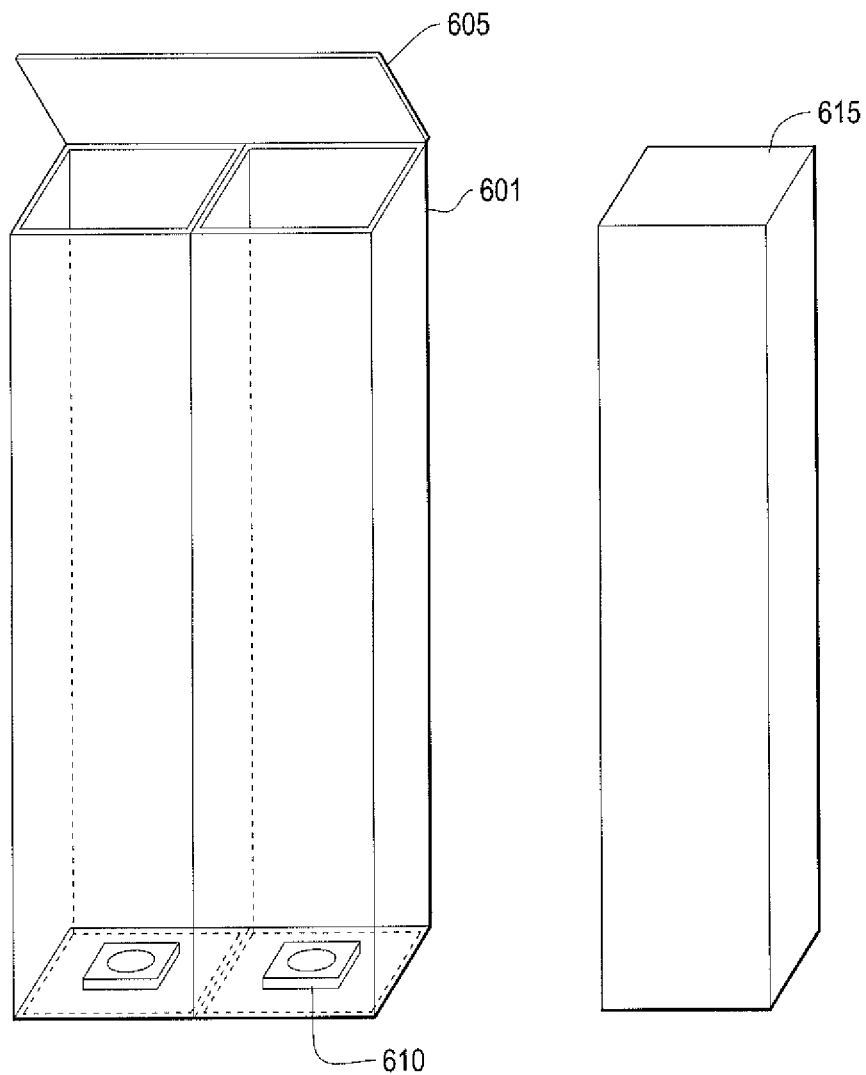
FIG. 4 is a perspective view of a medication monitor cartridge compartment in accordance with an exemplary embodiment.

FIG. 4 shows a medication cartridge. The medication cartridge may be constructed to be inserted into and/or removed from the medication monitor. The medication cartridge may be pre-filled with medication and/or refillable. The cartridge may accommodate any dosage form. In one version of the cartridge, 610 is a spring or other mechanism that keeps pushing stacked pills up so that one or more pills can be removed at a time when the cartridge is opened. In another version of the cartridge, 610 is a mechanism with an opening that allow one or more pills to be removed from the medication monitor. In this version, the spring or other mechanism may be contained in the package or magazine of stacked of pills. Either mechanism may also contain a sensor (optic or other) that senses when a pill is removed from the magazine or cartridge. A pre-fillable medication cartridge 615 according to embodiments is illustrated in FIG. 4. The pre-fillable medication cartridge 615 may have a specific shape to match a specific shape of a housing of the medication monitor. The monitor may include a sensor to detect, for example, an origin of manufacture and/or identity of contents of the pre-fillable medication cartridge 615. Each pre-fillable medication cartridge 615 may have a barcode, an RFID tag, or other information source that relays the origin of manufacture data and/or other data, for example to verify authenticity and/or identity of the medication. The monitor may also include a sensor to detect a specific shape of a medication, the specific shape of the pre-fillable medication cartridge 615, a medication made by a unique manufacturing process, or an orientation of the medication within the housing body as a way of protecting against counterfeiting and/or misuse of medication. The monitor may also include a barcode reader, an RFID label reader, or another information detector that allows for verifying whether the medication is counterfeit and/or the correct medication at the time of loading of the monitor and/or at the time of use by the patient. In addition to forwarding compliance data, the monitor may also send the information read by the reader to a receiving system such as a remote server, preferably the same remote server as discussed above, to verify whether the medication is authentic and/or the correct medication. The receiving system may compare the information received to the information in a database, and report issues to the patient and/or family, caretakers, support organizations, health care providers, etc.

The medication monitor may have one or more cartridges, which may or may not be separable as shown in FIG. 4. These multiple cartridges may hold the same drug (for example if higher doses or multiple pills are needed at a dose time) or different drugs. In one version there may be a mechanical mechanism in the medication monitor which slides past 610 of each cartridge, removing one or more pill (the pills can be different thicknesses and/or can be dispensed in groups) from each cartridge; the mechanism may be controlled mechanically or electromechanically. The magazine may be packaged with pills of existing shape and design, or pills may be designed with specific dimensions and characteristics allowing for pills to interface properly with packaging magazines, cartridges and/or medication monitors. The medication monitor may be configured to detect whether the pills provided in the magazine are authentic and appropriate, for example, by detecting any one or a combination of size, shape, color, unique manufacturing process of the pills, or unique manufacturing process of the pre-filled cartridge, as a barrier to counterfeiting or improper filling (e.g., with an incorrect medication). The outer housing of the pre-packed magazine of pills may have vapor or other barrier properties necessary to maintain the stability of the medication contained in them.

The algorithms used in methods, apparatus and systems described herein may be designed to determine a medication compliance pattern, or to analyze a medication compliance pattern received from the medication monitor 401. Further, the algorithms may be designed to correlate one or more patient medication compliance patterns with medication data and/or outcomes data, which also may be analyzed by way of the algorithms. Still further, the algorithms may analyze medication interaction data in view of medication data, outcomes data and medication compliance patterns to accommodate treatment regimen establishment and/or adjustment. Algorithms may also organize outcomes data, medication usage data, medication data, treatment regimen compliance patterns, and/or a combination thereof for presentation to a caretaker or other interested party. The organization may be effected by a ranking system in which values are attributed to aspects of the data to signify a level of importance to a caretaker or other interested party. For example, an output of an algorithm executed in accordance with an exemplary embodiment may be a warning that may be sent to at least one of a medication monitor 401, receiving system 410, server 420, and reporting system 430. The presentation may be textual, graphical, auditory, and/or diagrammatic. The data may be presented, for example, on a laptop, desktop or workstation computer display, or may be presented on a handheld device such as reporting system 430.

For example, an exemplary algorithm for methods, systems, and apparatus may include inputting a starting dosing regimen of a medication for treatment of a particular condition. Then, compliance patterns may be input. Medication data, medication properties data and patient history data may also be input. The algorithm may output, based on compliance patterns, medication data, medication properties data, and/or patient history data a new regimen or report.

An exemplary algorithm for methods, systems, and apparatus may include inputting medication data generated by obtaining a biological sample with a detection device, such as a skin-prick device, and detecting a presence and/or quantity of a target agent other than glucose in the biological sample through a glucose sensor.

For example, for a kidney transplant recipient (patient) with a safety risk of malignancy or infection, the algorithm may include the step of inputting a starting dosing regimen of cyclosporin A at x mg per day to provide post kidney transplant immunosuppression. The compliance pattern may be input, which may indicate that the patient has a pattern of high compliance with very few missed doses. The medication data, medication properties data and patient history data, including patient physical data (e.g., weight, body mass index, gender, etc.), patient cyclosporin A measurements, and other data, may be input. The algorithm may also consider malignancy and infection risk data linked to population compliance patterns. Taking these variables into account, the algorithm may then output a new treatment regimen that includes lowering a dose amount of the medication to y mg per day, for example, if compliance is low and/or target agent levels are high. Alternatively, the treatment regimen may be changed to one that is not correlated with malignancy or infection in view of the duration of the given patient's high compliance pattern and a desired level of target agent in the sample.

Over time, the database is populated with information from patients who have had malignancies or infections correlatable to variations among their individual compliance patterns. Specific compliance patterns and/or target agent levels that have a high probability of resulting in malignancies or infections are identified and are included in the algorithm. The algorithm routinely assesses each individual's ongoing compliance pattern and target agent levels. When an individual pattern is developing a correlation with a malignancies- or infections-related pattern, the algorithm outputs an appropriate and/or pre-established dose reduction and/or other treatment regimen change.

The algorithm may utilize models or subroutines in addition to assessing direct relationships between compliance patterns, target agent levels and malignancies or infections. For example, pharmacokinetic models (single compartment and others) can be utilized to project the resulting dynamic drug levels for the specific individual based on the specific individual's compliance pattern and medication data, allowing intervention to be engaged prior to a malignancy or infection event when projected drug exposure is too high. This approach can also be utilized with appropriate PK and/or ADME models when the patient is also prescribed other medications that may have drug-drug interactions such as inducing or inhibiting drug metabolism. As the database expands and includes existing and future biomarkers of malignancy or infections, the algorithm may establish relationships between individual compliance patterns and medication data and resulting changes in these biomarkers, allowing for the engagement of interventions (e.g., dose reduction) prior to a malignancy or infection event.

In another example, a compliance pattern may show that a patient occasionally misses doses but takes medication consistently and has stable but low target agent levels. The patient history data may show chronic rejection risk associated with the compliance pattern and/or target agent levels, and also show chronic allograft nephropathy data indicating histological tubulointestinal fibrosis and tubular atrophy. The algorithm may output a new dosing regimen that increases the dose, and/or the treatment regimen may be changed to one that is not correlated with chronic rejection with the given patient's specific compliance pattern and/or target agent levels.

Over time, the database is populated with information from patients who have had chronic rejection correlatable to variations among their individual compliance patterns and/or target agent levels. Specific compliance patterns and/or target agent levels that have a high probability of resulting in chronic rejection are identified and are included in the algorithm. The algorithm routinely assesses each individual's ongoing compliance pattern and/or target agent levels. When an individual pattern is developing a correlation with a chronic rejection-related pattern, the algorithm outputs an appropriate and/or pre-established dose increase and/or other treatment regimen change.

The algorithm may utilize models or subroutines in addition to assessing direct relationships between compliance patterns and/or target agent levels and chronic rejection. For example, pharmacokinetic models (single compartment and others) can be utilized to project the resulting dynamic drug levels for the specific individual based on the specific individual's compliance pattern and/or target agent levels, allowing intervention to be engaged prior to the chronic rejection. The intervention may be a behavioral intervention to change the individual's compliance pattern and/or dose amount and/or other treatment regimen changes (e.g., prohibiting administration of certain types of medications). As the database expands and includes existing and future biomarkers of chronic rejection, the algorithm may establish relationships between individual compliance patterns and resulting changes in these target agent levels, allowing for the engagement of interventions (e.g., dose increase) prior to a rejection event.

In another example, a patient with a risk of acute rejection may be given a starting dosing regimen of a drug for post kidney transplant immunosuppression. A compliance pattern that is input may show that the patient has had many missed doses and periods of missed doses. Medication data may show low or highly variable target agent levels. Medication properties data and patient history data may be input. The medication properties data, patient history data, and compliance pattern may be analyzed to determine and output an intervention prior to acute rejection of the transplanted kidney. For example, the intervention may be warning messages to the patient, family, support organizations; change of medications; change of dosage timing and/or amounts; and the like.

Over time, the database is populated with information from patients who have undergone acute rejection correlatable to variations among their individual compliance patterns and/or target agent levels. Specific compliance patterns and/or target agent levels that have a high probability of resulting in acute rejection are identified and are included in the algorithm. The algorithm routinely assesses each individual's ongoing compliance pattern and/or target agent levels. When an individual pattern is developing a correlation with an acute rejection-related pattern, the algorithm outputs an appropriate and/or pre-established intervention.

The algorithm may utilize models or subroutines in addition to assessing direct relationships between compliance patterns and/or target agent levels and acute rejection. For example, pharmacokinetic models (single compartment and others) can be utilized to project the resulting dynamic drug levels for the specific individual based on the specific individual's compliance pattern and/or target agent levels, allowing intervention to be engaged prior to the acute rejection event, for example when the drug exposure is too low or too intermittent. As the database expands and includes existing and future biomarkers (target agents) of acute rejection, the algorithm may establish relationships between individual compliance patterns and/or target agent levels and resulting changes in these biomarkers, allowing for the engagement of interventions prior to an acute rejection event.

The medication usage data, medication interaction data, outcomes data, medication data and medication compliance pattern(s) analyzed by the algorithms of the receiving system 410 may be made available to a patient's physician or other interested party by way of a secure website. A healthcare provider may understand a patient's individual medication compliance patterns and medication data and thereby perform informed establishment and/or adjustment of the patient's treatment regimen. Over time, as data builds on compliance patterns and/or target agent levels for populations of patients in specific disease states, such pattern data forms a registry that can provide profound insights into the relationship between patient medication compliance patterns and/or target agent levels and treatment regimens with individual patient medical outcomes or population medical outcomes. For example, such a database of patients with common disease indications can be a profound resource for improving public health and lowering the cost of medicine in specific disease states.

Using immunosuppressants in transplant as an example, over the past 20 years improvements in the kidney transplant and post transplant care process have improved 1-year graft survival rates, yet long term graft survival rates (5 years or greater) have not improved. A significant cause of the long term graft failures is declining medication compliance by individual patients. By utilizing methods, systems, and/or apparatus described herein, many of these long term graft failures can be prevented, avoiding the high cost of returning to dialysis and re-transplant.

A treatment regimen may be input to a processor, defined as taking two tablets per day, at 12 hour intervals—i.e., one tablet at 8:00 a.m. and one tablet at 8:00 p.m. The input regimen would include a window for each dose, such as plus or minus 30 minutes. The usage data from a monitor would show when each tablet was taken, for example by noting the time of opening of a single-tablet compartment in the monitor. The usage data could be communicated in real time, or stored and communicated in batches, to a compliance pattern processor. The compliance pattern processor could identify a pattern over time, e.g., one month, of, for example, timely, near-miss (e.g., within 30 minutes on one side of the window), distant-miss (e.g., between 30 minutes and two hours on one side of the window), and complete-miss doses. Preferably, the compliance pattern processor would also identify patterns of misses before the window and/or patterns of misses after the window. A treatment regimen processor would receive the compliance pattern. At the same or different intervals, patient fluid samples can be taken, for example, by a finger-prick device using the glucose meter, target agent levels in the sample can be determined. The target agent levels could optionally be correlated with the compliance pattern or considered separately. The processor would optionally also contain previously-stored patient history, medication properties, and other data, and could also continue to receive such data, and correlate it to associated compliance patterns. Upon correlating a new compliance pattern or medication data pattern to outcome data, for example, a pattern of increasingly distant misses and complete misses of the evening window but not of the morning window, and/or reduced morning target agent levels, to reduced efficacy of the tablets, it could generate an adjusted treatment regimen of one larger-dose, controlled release tablet to be taken only during the morning window. Outcomes data associated with this new treatment regimen could be input by, e.g., the patient's healthcare provider or by a diagnostic tool packaged with or part of a medication monitor, preferably tailored to a medication packaged with the monitor.

What has been described and illustrated herein are preferred embodiments of the invention along with some variations. The terms, descriptions and figures used herein are set forth by way of illustration only and are not meant as limitations. Those skilled in the art will recognize that many variations are possible within the spirit and scope of the invention.

What is claimed is:

1. A medication monitor comprising:
a housing configured to contain medication;
a detection device integrally formed into the housing, the detection device having a sample collection device and a target agent sensor for detecting a target agent in a biological sample from a user, wherein
the target agent sensor includes a plurality of sensors, where each sensor of the plurality of sensors comprises:
a solid support to which is attached a recognition molecule that specifically binds to the target agent in the presence of the target agent but not significantly to other agents,
a substance that can be enzymatically converted to glucose, and
an enzyme that can catalyze the conversion of the substance to glucose in the presence of the target agent, wherein
each sensor of the plurality of sensors being configured to detect a different target agent, and
at least one sensor of the plurality of sensors is configured to detect Tacrolimus or a metabolite thereof;
a processor configured to correlate the user's pattern of compliance with medication data and generate an adjusted treatment regimen upon identifying, based on an amount of glucose sensed, a pattern of misses in an initial treatment regimen; and
a communication port configured to communicate the medication data to a data network.

2. The medication monitor according to claim 1, wherein the housing includes a section for containing medication packaging, the housing defining an opening to accommodate insertion and removal of the medication packaging.

3. The medication monitor according to claim 2, further comprising:
a lid that opens to removably cover the opening;
a medication sensor that is configured to sense identity of the medication; and
a removal sensor that senses medication or medication packaging removal or device opening, wherein
the processor also produces medication data based on the sensed removal.

4. The medication monitor according to claim 1, wherein the sample collection device is a skin-prick device.

5. The medication monitor of claim 4, wherein the medication sensor is configured to sense an indicium of origin of manufacture of the medication to verify authenticity of the medication.

6. The medication monitor of claim 5, wherein the indicium of origin is provided by an information source associated with a pre-filled medication cartridge that is insertable into said opening.

7. The medication monitor of claim 6, wherein the housing includes a plurality of housings for containing a plurality of pre-filled medication cartridges.

8. The medication monitor of claim 6, wherein the information source is at least one member selected from the group consisting of an RFID chip, a barcode, and a shape of the cartridge.

9. The medication monitor according to claim 1, wherein the enzyme is attached to a Tacrolimus analogue molecule or a Tacrolimus metabolite analogue molecule that competes less strongly than Tacrolimus or the metabolite thereof for binding to the recognition molecule.

10. The medication monitor according to claim 1, wherein the enzyme is attached to a molecule that binds to Tacrolimus or a metabolite thereof that is bound to the recognition molecule.

11. The medication monitor of claim 1, wherein
the processor is configured to compare the amount of glucose sensed with a baseline glucose level and quantitatively determine an amount of the target agent present in the biological sample based on a difference between the baseline glucose level and the amount of glucose sensed.

12. The medication monitor of claim 1, wherein
the communication port is configured to output a recommendation to a health care provider to enable the health care provider to determine target drug levels or benchmark drug levels.

13. The medication monitor according to claim 1, wherein the solid support comprises a bead or a membrane.

14. The medication monitor according to claim 1, wherein
the communication port is configured to output a recommendation to a health care provider to enable the health care provider to determine target drug levels.

15. The medication monitor according to claim 1, wherein the enzyme is
an invertase, sucrase or sucrase-isomaltase that can convert sucrose to glucose,
a maltase that can convert maltose into glucose,
a trehalase that can convert trehalose into glucose,
an amylase that can convert starch into glucose, or
a cellulase that can convert cellulose into glucose.

16. The medication monitor according to claim 1, wherein the detection device is hard wired to the medication monitor.

17. The medication monitor according to claim 1, wherein the communications port is configured to wirelessly communicate the medication data to a data network.

18. A self-contained medication monitor comprising:
a housing body configured to contain medication;
a first detection device for detecting removal of medication from the self-contained medication monitor, the first detection device being integrally formed into the housing;
a second detection device having a target agent sensor for detecting a target agent in a biological sample from a user, the second detection device being integrally formed into the housing, wherein
the target agent sensor includes a plurality of sensors, where each sensor of the plurality of sensors comprises:
a solid support to which is attached a recognition molecule that specifically binds to the target agent in the presence of the target agent but not significantly to other agents;
a substance that can be enzymatically converted to glucose; and
an enzyme that can catalyze the conversion of the substance to glucose in the presence of the target agent;
a processor that produces medication usage data and medication data based on detected removal of the medication and an amount of glucose sensed and that outputs recommendations to the patient based on the medication usage data and medication data; and
a display device configured to display the recommendations to the patient;
wherein
each sensor of the plurality of sensors being configured to detect a different target agent, and at least one sensor of the plurality of sensors is configured to detect Tacrolimus or a metabolite thereof.

19. A method of optimizing treatment of a medication recipient patient, comprising:

generating usage data regarding a patient's compliance with a medication treatment regimen with the self-contained medication monitor of claim 18;

providing the usage data to a central server over a predetermined period of time;

determining the patient's pattern of compliance with the medication treatment regimen;

collecting a biological sample with a detection device that is operatively connected to the medication monitor;

sensing a target agent with a target agent sensor integrated onto the detection device, the target agent sensor including a plurality of sensors, where each sensor of the plurality of sensors comprises:

a solid support to which is attached a recognition molecule that permits detection of the target agent, wherein the recognition molecule specifically binds to the target agent in the presence of the target agent but not significantly to other agents;

a substance that can be enzymatically converted to glucose;

an enzyme that can catalyze the conversion of the substance to glucose in the presence of the target agent; and detecting the glucose produced from the substance with a glucose meter to generate medication data, wherein the detection of glucose indicates a presence of the target agent in the biological sample, and an absence of detected glucose indicates an absence of the target agent in the biological sample;

correlating the patient's pattern of compliance with the medication data and identifying, based on the detection of glucose, a pattern of misses in an initial treatment regimen; and outputting at least one recommendation selected from the group consisting of:

changing at least one dosage of at least one medication used in the treatment regimen, and changing the timing of recommended usage of at least one medication in the treatment regimen; wherein the target agent comprises Tacrolimus or a metabolite thereof.

20. The self-contained medication monitor according to claim 18, wherein the processor is configured to compare the amount of glucose sensed with a baseline glucose level and quantitatively determine an amount of each target agent present in the biological sample based on a difference between the baseline glucose level and the amount of glucose sensed.

* * * * *